United States Patent
Hayakawa et al.

[11] Patent Number: 5,926,869
[45] Date of Patent: Jul. 27, 1999

[54] TABLE

[75] Inventors: Kazuhiko Hayakawa; Katsumasa Nose, both of Tokyo, Japan

[73] Assignee: GE Yokogawa Medical Systems, Limited, Tokyo, Japan

[21] Appl. No.: 08/963,229

[22] Filed: Nov. 3, 1997

[30] Foreign Application Priority Data

Feb. 24, 1997 [JP] Japan ................................ 9-038970

[51] Int. Cl.⁶ .......................................................... A61B 6/02
[52] U.S. Cl. ................................ 5/81.1 R; 5/425; 5/429; 5/430; 5/601
[58] Field of Search ................................ 5/81.1 R, 86.1, 5/81.1 HS, 625, 601, 429, 430, 426, 425; 378/208, 209; 600/410

[56] References Cited

U.S. PATENT DOCUMENTS

| | | | |
|---|---|---|---|
| 3,905,591 | 9/1975 | Schorr et al. | 5/601 |
| 4,613,122 | 9/1986 | Manabe | 5/601 |
| 5,053,042 | 10/1991 | Bidwell | 378/208 X |
| 5,199,060 | 3/1993 | Kato | 378/208 X |
| 5,609,763 | 3/1997 | Randolph et al. | 5/601 |

*Primary Examiner*—Michael F. Trettel
*Assistant Examiner*—Fredrick Conley
*Attorney, Agent, or Firm*—Moonray Kojima

[57] ABSTRACT

In order to improve the operational efficiency and mitigate the burden for a subject, there is provided a table comprising a table body 41 which can be moved upwardly and downwardly, and a cradle 42 disposed over the table body 41 and having a cradle body portion 42c on which the subject 30 is to be mounted and an extending portion (first extending portion) 42a projecting laterally from at least one lateral portion of the cradle body portion 42c and extending to the vicinity of a mat 32 on a carrying means (stretcher) 25 alongside, the extending portion 42a being for use in shifting the subject 30 on the carrying means 25 to the cradle body portion 42c.

1 Claim, 4 Drawing Sheets

TABLE

BACKGROUND OF THE INVENTION

The present invention relates to a table disposed in an MR (Magnetic Resonance) apparatus, a radiation CT (Computed Tomography) apparatus or the like. The term "radiation" implicates X-ray, gamma-ray or the like.

An MR apparatus or a radiation CT apparatus is provided with a table which carries a subject into a bore of a gantry.

When the subject which is not self-supportedly ambulant is examined by such an apparatus, a carrier, for example, a bed having wheels referred to as a stretcher, is used to carry the subject, and the stretcher is brought alongside the table in such an apparatus to shift the subject to the table.

FIG. 1 illustrates the operation for shifting the subject, wherein reference numeral 2 designates a table disposed adjacent to an MR apparatus body. The table 2 consists of a table body 3 which can be moved upwardly and downwardly (in the direction indicated by an arrow I in FIG. 1), and a cradle 4 which is disposed over the table body 3 and is horizontally movable, for carrying the subject mounted thereon into the bore of the MR apparatus body.

Reference numeral 5 designates a stretcher for carrying a subject 10 which is not self-supportedly ambulant, to the table 2. The subject 10 is mounted on the stretcher 5 with a mat 12 placed between the subject 10 and the stretcher 5. The lateral portion of a mounting surface for the mat 12 of the stretcher 5 is provided with handrails 6 and 7 for preventing the subject 10 from falling off. The proximal ends 6a and 7a of the handrails 6 and 7 are pivotally attached to the stretcher 5, and the handrails 6 and 7 is allowed to have two modes, one of which is the operative mode in which their rotating distal ends extend upwardly (the mode of the handrail 7: the mode for preventing the subject 10 from falling off), and another of which is the release mode in which their rotating distal ends extend downwardly (the mode of the handrail 6).

With regard to the table 2, since the width of the cradle 4 is no more than the breadth of the subject's shoulder, an envelope portion 3a is formed on the table body 3 which turns up to the lateral portion of the cradle 4, and aids the ambulant subject 10 to climb on the cradle 4 alone.

The table 2 and the stretcher 5 is used as follows.

While the subject 10 is carried by the stretcher 5, both handrails 6 and 7 are set to the operative mode, preventing the subject 10 from falling off the stretcher 5. Prior to bringing the stretcher 5 alongside the table 2, the handrail on the side adjacent to the lateral surface of the table 2 (the handrail 6 in this case) is set to the release mode and the stretcher 5 is brought alongside the table 2.

Next, an operator 11 moves the table body 3 up and down so that the cradle 4 is positioned at generally the same height as the mounting surface for the mat 12 of the stretcher 5.

The operator 11 then climbs on a step 13 on the floor on the side opposite to the side of the table 2 which the stretcher 5 is brought alongside, with one foot put on the cradle 4 of the table 2, holding the lateral portion of the mat 12 on which the subject is mounted, and shifts the subject 10 along with the mat 12 to the cradle 4 of the table 2.

In the above-constructed table 2, since the envelope portion 3a is formed, there is provided a distance (L) from the lateral portion of the table 2 to the cradle 4. On the other hand, the proximal end 6a of the handrail 6 on the stretcher 5 also protrudes in the width direction. Accordingly, even if the stretcher 5 is brought alongside the lateral portion of the table 2 as close as possible, the shift distance for the subject 10 to the cradle 4 is prolonged, resulting in the poor operational efficiency for the operator 11.

Also, the proximal end 6a of the handrail 6 protrudes above the mounting surface for the mat 12 of the stretcher 5. Therefore, the operator 11 pulls the mat 12 with the lateral portion of the mat 12 on the side of the table 2 lifted up aslant in order to get over the proximal end 6a of the handrail 6. Lifting up the mat 12 aslant forces the subject 10 to change its position. Moreover, the long pulling distance makes the burden heavy for the subject 10 which suffers from some disease such as spine injury or fracture.

SUMMARY OF THE INVENTION

It is an object of the present invention to provide a table which offers the good operational efficiency for the operator and mitigates the burden for the subject in shifting the subject from a carrying means.

According to a first aspect of the present invention, there is provided a table characterized by comprising a table body which can be moved upwardly and downwardly, and a cradle disposed over said table body and having a cradle body portion on which the subject is to be mounted and an extending portion projecting laterally from at least one lateral portion of said cradle body portion and extending to the vicinity of a mat on a carrying means when said carrying means is brought alongside, said extending portion being for use in shifting the subject on said carrying means to said cradle body portion.

First, the table body is lifted up and the extending portion of the cradle is positioned higher than a subject mounting surface of the carrying means such as the stretcher.

Next, the carrying means is brought alongside the table with the lateral portion of the carrying means sinking under the extending portion of the cradle, and thereafter, the table body is lowered so that the upper surface of the extending portion of the cradle is positioned at generally the same height as the subject mounting surface of the mat disposed on the carrying means.

Then the subject on the mat on the carrying means is shifted via the extending portion to the cradle body portion.

According to the above arrangement, by sinking the lateral portion of the carrying means under the extending portion of the cradle and lowering the table body, the upper surface of the extending portion and the subject mounting surface of the mat have generally the same height and the distance between the cradle body portion of the cradle and the subject on the carrying means is reduced.

Therefore, the subject can be carried generally in parallel manner and is not forced to change its position, which mitigates the burden for the subject.

In addition, the carrying distance is reduced, which improves the operational efficiency for the operator and mitigates the burden for the subject since the carrying time is reduced.

According to a second aspect of the present invention, there is provided the table in accordance with the first aspect, characterized in that said extending portion is disposed on either lateral portion of said cradle body portion.

Because the extending portion is disposed on either lateral portion of said cradle body portion, the installation site of the MR or CT apparatus etc. is unrestricted, and the carrier on which the subject is mounted is allowed to be placed alongside the table at the shortest distance, hence offering the good operational efficiency for the operator.

According to a third aspect of the present invention, there is provided the table in accordance with said first and second aspects, characterized by comprising a guard having a portion extending upwardly from the vicinity of the lateral portion of said cradle while the subject is mounted on said cradle body portion, the guard being put aside within a space between said extending portion and a floor on which the table is situated, which space does not interfere with said carrying means alongside while shifting the subject on said carrying means to said cradle body portion.

When the guard is operative, it has a portion extending upwardly from the vicinity of the lateral portion of the subject mounting surface of the cradle, thus preventing the subject mounted on the cradle from falling off.

When the guard is put aside, it is positioned within a space between the extending portion of the cradle and the floor, which space does not interfere with the subject carrying means alongside, thus allowing the subject mounting portion of the carrier to be brought alongside the table, reducing the subject shifting distance and offering the good operational efficiency for the operator.

Furthermore, the carrying time is reduced, which also mitigates the burden for the subject.

One embodiment of the arrangement of the guard includes a guard consisting of a rotational trunk portion pivotally attached to the lateral portion of said table body and a crank portion bent at the tip portion of said rotational trunk portion, the crank portion, when said rotational trunk portion is generally horizontal, being set so that said crank portion is positioned at the lateral portion of the extending portion of said cradle and its tip extends upwardly above said extending portion, and, when the rotational trunk portion is generally vertical, being set so that its tip does not project laterally beyond the extending portion of said cradle.

Further objects and advantages of the present invention will be apparent from the following description of the preferred embodiments of the invention as illustrated in the accompanying drawings.

DETAILED DESCRIPTION OF THE INVENTION

The mode for carrying out the present invention will hereinafter be described with reference to the accompanying drawings.

Figure 3:
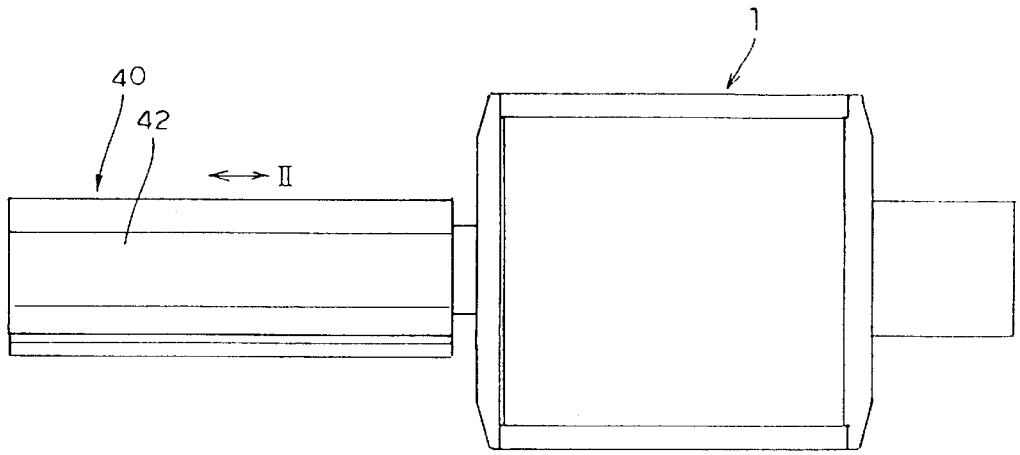
FIG. 3 is a top plan view of the MR apparatus.
Figure 4:
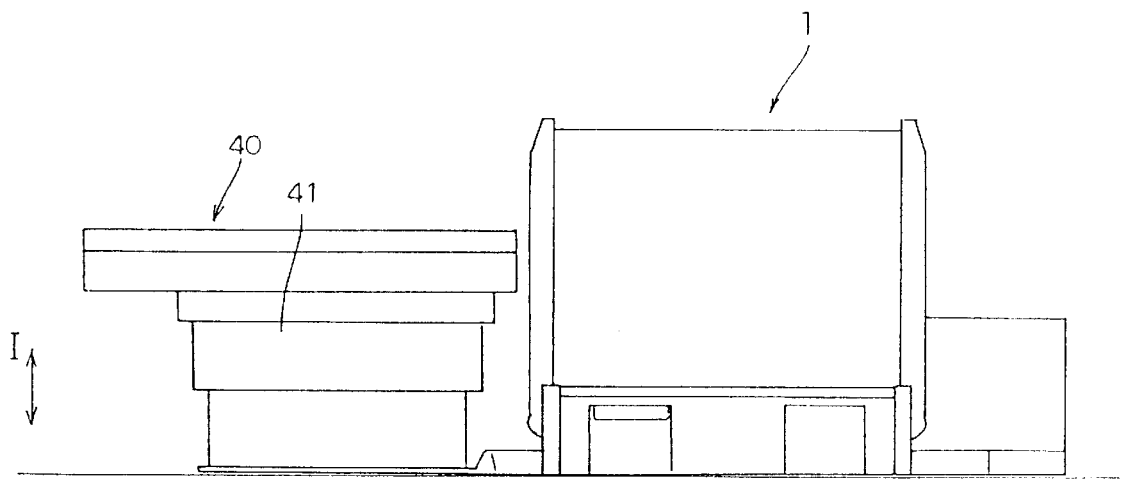
FIG. 4 is an elevational view of the MR apparatus.
Figure 5:
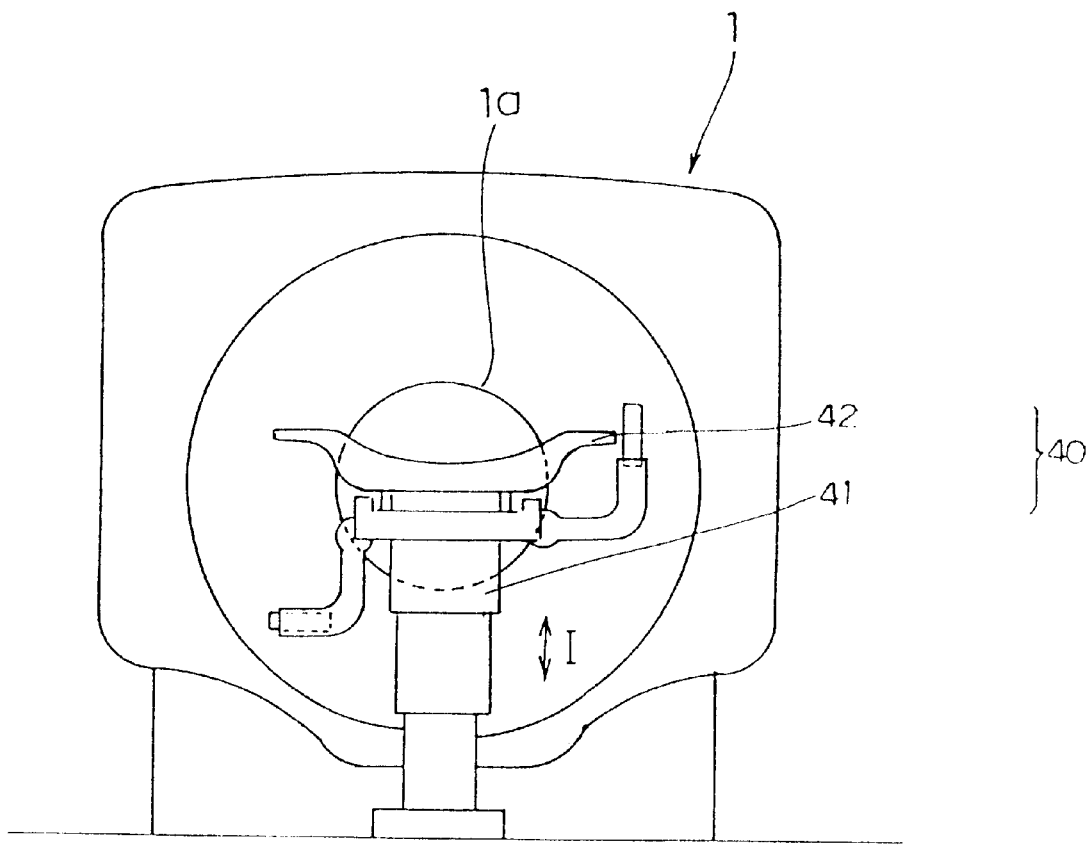
FIG. 5 is an enlarged view illustrating the left side of the apparatus shown in FIG. 3.

The general arrangement of an MR apparatus will now be described in which one embodiment of the table in accordance with the present invention is used, with reference to the FIGS. 3–5. In FIG. 5, reference numeral 1 designates an MR apparatus body which is provided with a bore 1a through which a subject is inserted, and reference numeral 40 designates a table disposed adjacent to the MR apparatus body 1. The table 40 consists of a table body 41 which can be moved upwardly and downwardly (in the direction indicated by arrow I in FIGS. 4 and 5), and a cradle 42 which is disposed over the table body 41 and is horizontally movable (in the direction indicated by arrow II in FIG. 3), for carrying the subject mounted thereon through the bore 1a of the MR apparatus body 1.

Figure 1:
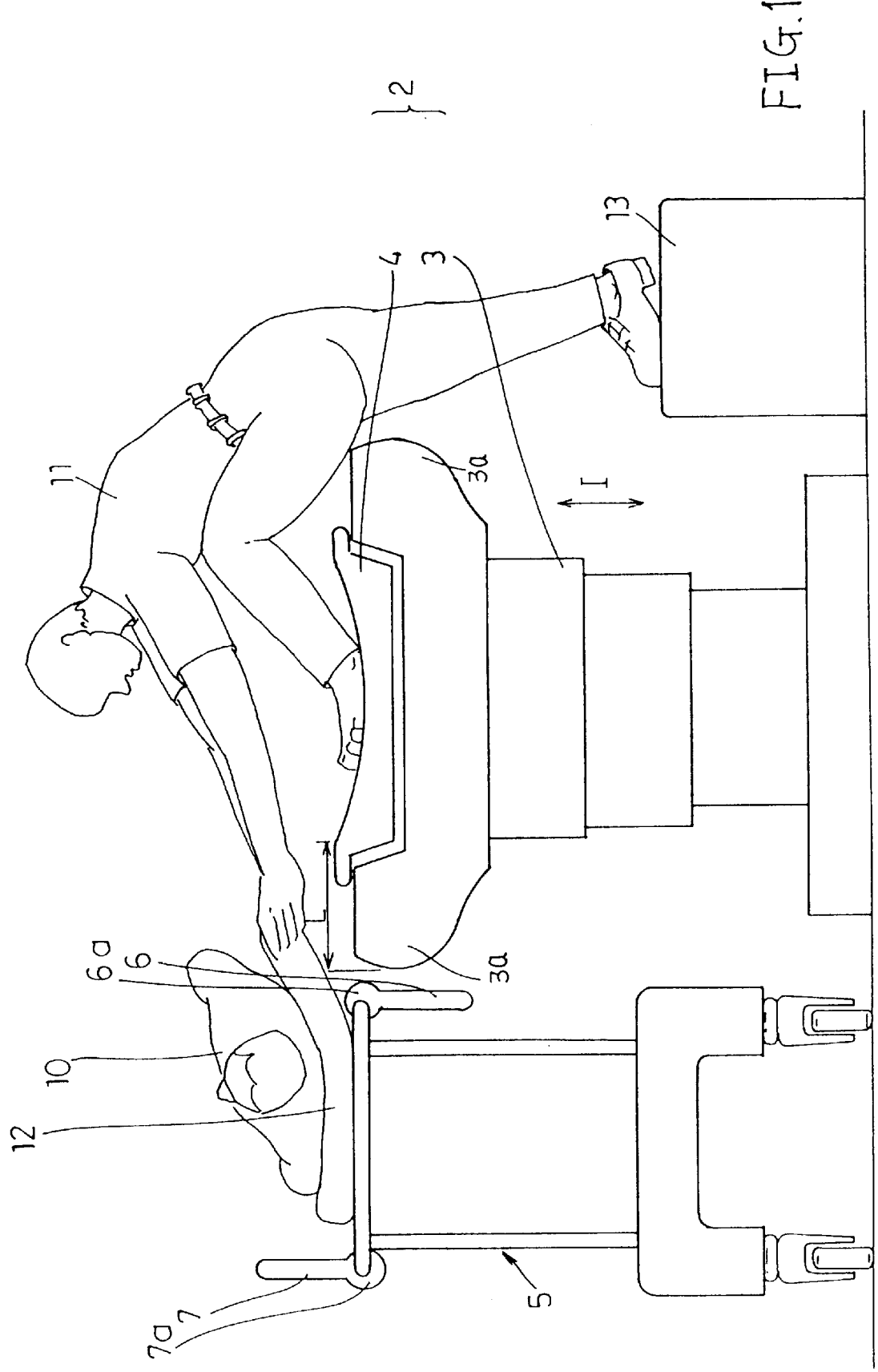
FIG. 1 illustrates an arrangement of the prior art.
Figure 2:
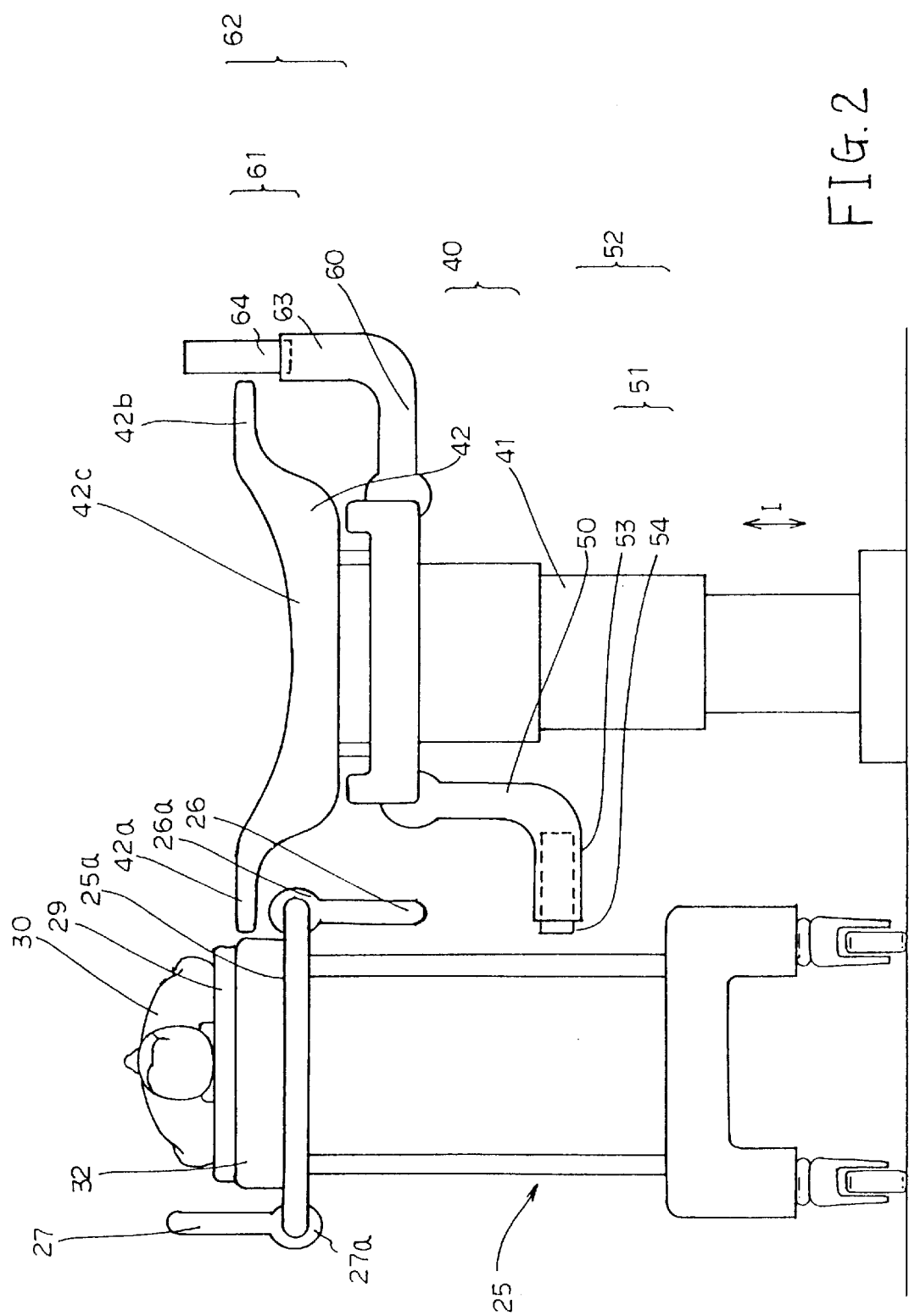
FIG. 2 illustrates an arrangement in accordance with one embodiment of the present invention.

Next, the table 40 will be described in more detail with reference to FIG. 2. FIG. 2 illustrates an arrangement of the table which is one embodiment of the present invention.

In the drawing, a subject 30 is mounted with a mat 32 and a mat 29 placed between the subject 30 and the subject mounting surface 25a, the mat 32 being disposed on a subject mounting surface 25a of the stretcher 25, and the mat 29 having a good slidability and being disposed on the mat 32. The lateral portions of the mounting surface for the mat 32 of the stretcher 25 is provided with handrails 26 and 27 for preventing the subject 30 from falling off. The proximal ends 26a and 27a of the handrails 26 and 27 are pivotally attached to the stretcher 25, and the handrails 26 and 27 are allowed to have two modes, one of which is the operative mode in which their rotating distal ends extend upwardly (the mode of the handrail 27: the mode for preventing the subject 30 from falling off), and another of which is the release mode in which their rotating distal ends extend downwardly (the mode of the handrail 26).

The cradle 42 of the table 40 consists of a cradle body portion 42c on which the subject 30 is to be mounted, a first extending portion 42a formed on one lateral portion of the cradle body portion 42c, extending laterally further from that lateral portion of the table body 41 to the vicinity of the mat 32 on the stretcher 25 alongside on which the subject is mounted, and a second extending portion 42b formed on another lateral portion of the cradle body portion 42c, extending laterally further from that lateral portion of the table body 41 to the vicinity of the mat 32 on the stretcher 25 alongside on which the subject is mounted.

In addition, one lateral portion of the table 41 is provided with a first guard 52 consisting of a rotational trunk portion 50 pivotally attached to that lateral portion of the table 41, and a crank portion 51 bent at the tip of the rotational base portion 50. Further, the crank portion 51 consists of a connecting portion 53 associated with the rotational trunk portion 50, and a slide portion 54 which can be contained within or protruded from the connecting portion 53.

Another lateral portion of the table 41 is provided with a second guard 62 consisting of a rotational trunk portion 60 pivotally attached to that lateral portion of the table 41, and a crank portion 61 bent at the tip of the rotational base portion 60. Further, the crank portion 61 consists of a connecting portion 63 associated with the rotational trunk portion 60, and a slide portion 64 which can be contained within or protruded from the connecting portion 63.

The first and second guards 52 and 62 can be moved in motorized manner or manually between two positions, one of which is in the operative mode in which the rotational trunk portion is generally horizontal (the mode of the second guard 62 in the drawing), and another of which is the put-aside mode in which the rotational trunk portion is generally vertical (the mode of the first guard 52 in the drawing).

The operation of the above arrangement will now be described. While the subject 30 is carried by the stretcher 25, both handrails 26 and 27 are in the operative mode, preventing the subject 30 from falling off the stretcher 25. Prior to bringing the stretcher 25 alongside the table 40, the handrail on the side adjacent to the lateral surface of the table 40 (the handrail 26 in this case) is set to the release mode.

On the other hand, with regard to the table 40, the guard on the side which the stretcher 25 is brought alongside, i.e., the first guard 52 in this embodiment, is also set to the put-aside mode. At this time, the slide portion 54 of the crank portion 51 is contained within the connecting portion 53 so that the tip of the crank portion 51 does not protrude laterally beyond the first extending portion 42a.

When the first guard 52 is in the put-aside mode, the space which accommodates the subject mounting surface 25a of the stretcher 25 is formed between the first extending portion 42a of the cradle 42 and the crank portion 51 of the first guard 52.

And the table 41 is lifted up so that the first extending portion 42a of the cradle 42 is positioned higher than the subject mounting surface 25a of the stretcher 25.

Next, the stretcher 25 is brought alongside the table 40 with the lateral portion of the stretcher 25 sinking under the first extending portion 42a of the cradle 42, and thereafter, the table body 41 is lowered so that the upper surface of the first extending portion 42a of the cradle 42 is positioned at generally the same height as the subject mounting surface of the mat 32 disposed on the stretcher 25.

The mat 29 having a good slidability is then pulled to shift the mat 29 and the subject 30 via the first extending portion 42a of the cradle 42 to the cradle body portion 42c.

According to the above arrangement, by sinking the lateral portion of the stretcher 25 under the first extending portion 42a of the cradle 42 and lowering the table body 41, the upper surface of the first extending portion 42a and the subject mounting surface of the mat 32 have generally the same height and the distance between the cradle body portion 42c of the cradle 42 and the subject 30 on the stretcher 25 is reduced.

Therefore, the subject 30 can be carried generally in parallel manner and is not forced to change its position, which mitigates the burden for the subject.

Also, the carrying distance is reduced, which improves the operational efficiency for the operator and mitigates the burden for the subject since the carrying time is reduced.

Moreover, and according to the present embodiment, because the first and second extending portions 42a and 42b are formed on the respective sides of the cradle 42, the installation site of the MR apparatus is unrestricted, and the stretcher 25 on which the subject 30 is mounted is allowed to be brought alongside the table 40 at the shortest distance, hence offering the good operational efficiency for the operator.

Also, because the first and second guards 52 and 62 are disposed at the table body 41, the subject 30 mounted on the cradle 42 is prevented from falling off by the guards 52 and 62 in the operative mode.

The present invention is not limited to the above embodiment. In the above embodiment, the mat 29 having a good slidability is used on the mat 32, but the towels or the like may be used. Furthermore, the first and second guards 52 and 62 in the operative mode can serve as the arm rest for the subject 30 under infusion.

Many widely different embodiments of the invention may be constructed without departing from the spirit and the scope of the present invention. It should be understood that the present invention is not limited to the specific embodiment described in the specification, except as defined in the appended claims.

We claim:

1. A table comprising:
   a body movable in a vertical direction;
   a top portion disposed on top of said body and comprising two parallel sides and transverse thereto two ends;
   a pair of guards disposed on said parallel sides, each comprising:
      a base rotatably attached to said sides;
      an L-shaped arm extending from said base; and
      an extended portion retractable into said L-shaped arm, whereby in an upright position said guard extends upward from said top portion with said extended portion extending verically from said L-shaped arm, and in a downward position said guard extends downward from said top portion with said extended portion retracted into said L-shaped arm; and
   a cradle body disposed in said top portion, said cradle body comprising a pair of lips and a depressed portion therebetween with said pair of lips extending toward said parallel sides of said top portion, said cradle body being movable horizontally in a direction toward said ends and in a direction toward said parallel sides.

* * * * *